May 30, 1961 D. H. MOREY, JR Plant Pat. 2,059
ROSE PLANT
Filed Sept. 26, 1960
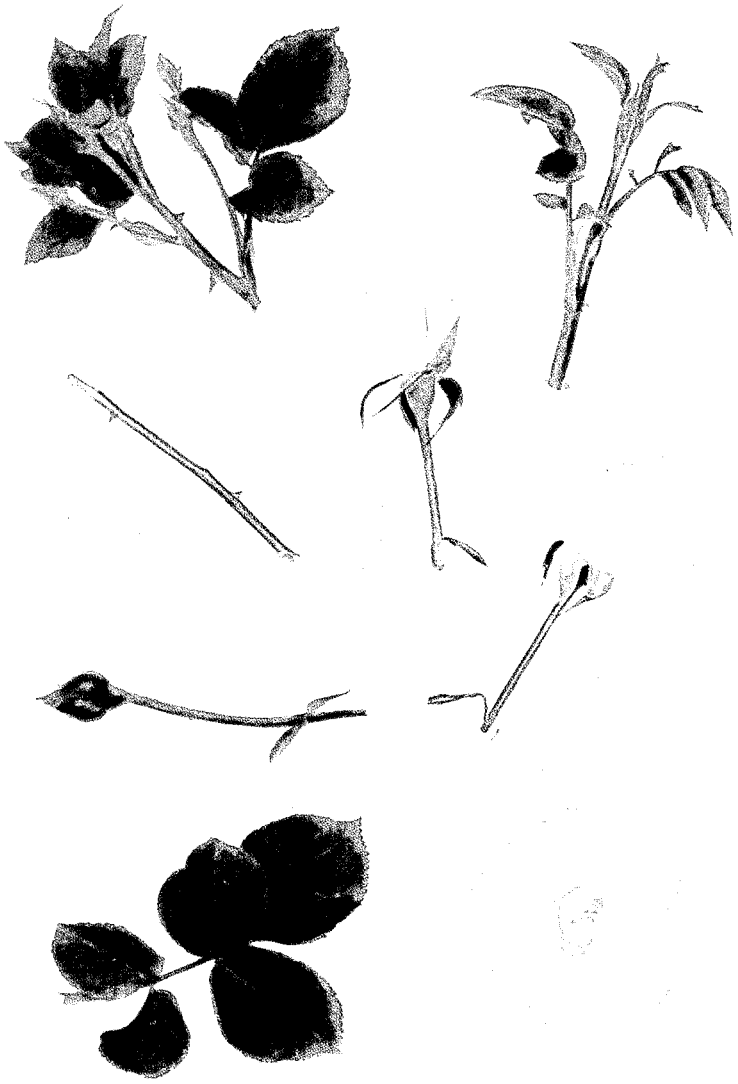
Inventor.
Dennison H. Morey, Jr.
By: Robb & Robb
Attorneys.

United States Patent Office

Plant Pat. 2,059
Patented May 30, 1961

2,059

ROSE PLANT

Dennison H. Morey, Jr., Pleasanton, Calif., assignor to Jackson & Perkins Company, Newark, N.Y., a corporation of New York Filed Sept. 26, 1960, Ser. No. 58,587

1 Claim. (Cl. 47—61)

The present invention relates to a new and distinct variety of rose plant of the floribunda class, which was originated by me by crossing an unnamed and unpatented seedling of "Navajo" (unpatented) ×"Golden Dawn" (unpatented) with the variety "Pinocchio" (Plant Patent No. 484).

The primary objective of this breeding was to produce a new rose variety which has the desirable characteristics of the parent variety "Pinocchio," but which combines therein a lower growing habit and a more intensified flower color. This objective was fully achieved, along with other desirable improvements, as evidenced by the following unique combination of characteristics which are outstanding in the new variety and which distinguish it from its parents, as well as from all other varieties of which I am aware:

(1) A compact plant habit, with attainment of a plant height of about only 2 feet;

(2) Free blooming habit; and (3) A unique and distinctive Geranium Pink general color tonality of the flowers, with the center of the flower petals overcast with light Salmon Orange.

Asexual reproduction of the new variety by budding, as performed at Pleasanton, California, and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling of "Navajo" ×"Golden Dawn."

*Pollen parent.*—"Pinocchio."

Classification:

*Botanic.*—Floribunda.

*Commercial.*—Floribunda.

*Flower*

(Observations made from specimens grown outdoors at Newark, New York, about mid-afternoon in the latter part of the month of August.)

Blooming habit: Recurrent—continuous; very free blooming.

Bud:

*Size.*—Small.

*Form.*—Ovoid; is not affected by wet or hot weather.

*Color.*—When sepals first divide—Begonia Rose, Plate 1. When petals begin to unfurl—Geranium Pink, Plate 1, with lower half of petals lightly overcast with light Orange Yellow, Plate 3. When half-blown: inside of petals—Eosine Pink, Plate 1, with outer edge of petals lightly overcast with Marguerite Yellow, Plate 30; reverse of petals—Ivory Yellow, Plate 30, with outer edge of petals lightly overcast with Strawberry Pink, Plate 1.

*Sepals.*—Branched; curl back when petals begin to unfurl. Color: inside—deep Lichen Green, Plate 33; outside—Chromium Green, Plate 32.

*Calyx.*—Color—Biscay Green, Plate 17. Shape—pear. Size—small. Aspect—smooth. Odor when rubbed—none.

*Peduncle.* — Length — short. Aspect — rough. Strength—erect; slender. Color—Biscay Green, Plate 17.

*Opening.*—Opens up well; is not affected by adverse weather conditions.

Bloom:

*Size.*—Small. Average size when fully expanded—from 2½ inches to 3 inches.

*Borne.*—Several together and in rounded clusters.

*Stems.*—Short; normal strength.

*Form (when first open).*—Open. Permanence—retains its form to the end.

*Petalage.*—Double (full but open center). Number of petals under normal conditions—20.

*Color.*—Center of flower—Eosine Pink, Plate 1, lightly overcase with Bittersweet Pink, Plate 2. Outer petals—Geranium Pink, Plate 1, lightly overcast with Grenadine Pink, Plate 2. Base of petals (aiglet)—Empire Yellow, Plate 4. Inside of petals—Geranium Pink, Plate 1, with the center of the petals overcase with light Salmon Orange, Plate 2. Reverse of petals—Maize Yellow, Plate 4, with outer edge of petals lightly overcast with Grenadine Pink, Plate 2. General tonality from a distance—Geranium Pink, Plate 1, lightly overcast with light Salmon Orange, Plate 2.

*Discoloration.*—General tonality at end of first day—Eosine Pink, Plate 1, lightly overcast with Bittersweet Pink, Plate 2. Second day—Geranium Pink, Plate 1, with center of the petals overcast with light Salmon Orange, Plate 2. Third day—Geranium Pink, Plate 1, lightly overcast with Grenadine Pink, Plate 2.

Petals:

*Texture.*—Thin; is not affected by wet or hot weather.

*Appearance.*—Inside—satiny. Outside—shiny.

*Form.*—Round.

*Arrangement.*—Informal (with "rags" in center).

*Petaloids in center.*—Few; small.

*Persistence.*—Drop off cleanly.

*Fragrance.*—Moderate. Nature—tea (average hybrid tea scent.

*Lasting quality.*—On the plant—long. As cut flower—long.

*Genital organs*

*Stamens, anthers*: Small; many; regularly arranged around styles. Color—Apricot Yellow, Plate 4.

*Stamens, filaments* (threads): Short. Color—Picric Yellow, Plate 4.

*Pollen*: Color—Maize Yellow, Plate 4.

*Styles*: Bunched; uneven length; short; thin.

*Stigmas*: Color—Primrose Yellow, Plate 30.

*Ovaries*: All enclosed in calyx.

*Hips*: None.

*Seeds*: None.

*Plant*

*Form*: Bush.

*Growth*: Vigorous; upright; compact; attains height of only about 2 feet.

Foliage: Compound of 3–5 leaflets.

*Size.*—Medium.

*Quantity.*—Normal.

*Color.*—New foliage: upper side—Calla Green, Plate 5, lightly overcast with Victoria Lake, Plate 1; under side—Neutral Red, Plate 38. Old foliage: upper side—Varley's Green, Plate 18; under side light Hellebore Green, Plate 17.

*Shape.*—Oval.

*Texture.*—Upper side—leathery. Under side—smooth.

*Ribs and veins.*—Ordinary.

*Edge.*—Serrated (saw-toothed).

*Serration.*—Both double and single; small.

*Leaf stem.*—Color—Absinthe Green, Plate 31. Under side—prickly.

*Stipules.*—Medium length; bearded.

Wood:

*New wood.*—Color—Parrot Green, Plate 6. Bark—smooth.

*Old wood.*—Color—Cress Green, Plate 31. Bark—smooth.

Thorns:

*Thorns.*—Quantity: on main stalks from base—few; on laterals from stalk—few. Form—narrow base; medium length; straight. Color (when young)—Begonia Rose, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of the general characteristics of the variety "Pinocchio" (Plant Patent No. 484), but having a more compact plant habit, a very free blooming habit, and a unique and distinctive Geranium Pink general color tonality of the flowers, with the center of the flower petals overcast with light Salmon Orange.

No references cited.